United States Patent
Philippe et al.

(10) Patent No.: US 6,214,325 B1
(45) Date of Patent: Apr. 10, 2001

(54) HYDROXYPROPYL QUATERNARY AMMONIUM COMPOUNDS CONTAINING AN ESTER FUNCTION, AND COSMETIC AND DERMATOLOGICAL COMPOSITIONS CONTAINING THEM

(75) Inventors: Michel Philippe, Wissous; Alain Campos, Mitry Mory; Didier Semeria, Courtry, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/988,534

(22) Filed: Dec. 10, 1997

(30) Foreign Application Priority Data

Dec. 11, 1996 (FR) .................................... 96 15224

(51) Int. Cl.$^7$ ...................................... A61K 7/06

(52) U.S. Cl. .......................... 424/70.1; 514/880; 514/881

(58) Field of Search ................... 424/401, 70.1, 424/70.28, 70.5; 514/844–846, 529, 880, 881; 554/1, 108; 560/155; 564/292; 510/123, 124, 125

(56) References Cited

U.S. PATENT DOCUMENTS

| | | | |
|---|---|---|---|
| 3,272,712 | * 9/1966 | Kalopsis et al. | 167/87 |
| 3,342,840 | 9/1967 | Sobolev | 260/404 |
| 3,872,138 | 3/1975 | Ogata | 260/404 |
| 4,173,539 | 11/1979 | Rule et al. | 252/8.8 |
| 4,840,738 | 6/1989 | Hardy et al. | 252/8.6 |

FOREIGN PATENT DOCUMENTS 1313143   5/1963   (FR) .

OTHER PUBLICATIONS

Derwent Abstract of DE–A–1793834, Oct. 21, 1976.

* cited by examiner

*Primary Examiner*—Diana Dudash
*Assistant Examiner*—Michael G. Hartley
(74) *Attorney, Agent, or Firm*—Finnegan, Henderson, Farabow, Garrett & Dunner, L.L.P.

(57) ABSTRACT

Hydroxypropyl quaternary ammonium compounds containing an ester function, in particular containing a fatty acid ester function, of formula (I):

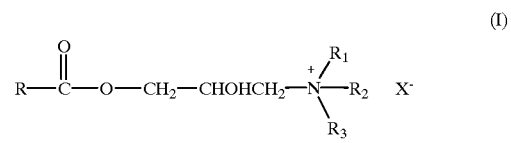

in which R denotes a branched $C_7$–$C_{35}$ alkyl chain;

$R_1$, $R_2$ and $R_3$ independently denote a $C_1$–$C_{18}$ alkyl chain;

$X^-$ denotes a halide or another anion chosen from:

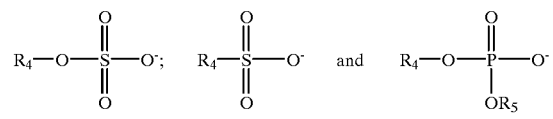

in which $R_4$ and $R_5$ independently denote a $C_1$–$C_8$ alkyl chain are disclosed. Cosmetic or dermatological compositions containing these compounds, in particular haircare products in which the quaternary compounds are used as treatment agents for improving the surface condition of the hair as well as for protecting the hair under the action of atmospheric agents or mechanical or chemical treatments are disclosed.

1 Claim, No Drawings

HYDROXYPROPYL QUATERNARY AMMONIUM COMPOUNDS CONTAINING AN ESTER FUNCTION, AND COSMETIC AND DERMATOLOGICAL COMPOSITIONS CONTAINING THEM

The present invention relates to novel hydroxypropyl quaternary ammonium derivative compounds containing an ester function, in particular a fatty acid ester function, as well as to their uses in cosmetic or dermatological products, especially in haircare and hair treatment products.

It is well known that hair that has been sensitized, i.e. damaged and/or made brittle, to varying degrees under the action of atmospheric agents or under the action of mechanical or chemical treatments, such as dyeing, bleaching and/or permanent-waving operations, is often difficult to disentangle, and to style, and lacks softness.

This is because, under the action of these attacking factors, i.e., atmospheric agents and mechanical or chemical treatments, the hair loses some of its constituents such as, in particular, proteins.

Certain quaternary ammonium compounds have been known for many years in haircare products as hair conditioners that facilitate disentangling and combing of the hair and that provide softness to the hair. Cetyltrimethylammonium bromide and behenyltrimethylammonium bromide are known in particular for these purposes.

Certain hydroxypropyl quaternary ammonium compounds containing a fatty acid ester function are also known as hair conditioners which impart sheen and a soft feel and facilitate the combing and disentangling of the hair. These compounds are described in French Patent No. FR 1,313,143.

The inventors have discovered, surprisingly, a novel family of hydroxypropyl quaternary ammonium derivative compounds containing an ester function, in particular a fatty acid ester function, which will be defined in greater detail below, which make it possible, after they are applied to the hair, to obtain hair with a substantially smoother surface condition and to improve considerably the combing and disentangling of the hair, when compared with the quaternary derivatives commonly used in haircare formulations.

The hydroxypropyl quaternary derivative compounds containing an ester function of the invention also make it possible to obtain good protection of the skin and/or hair fibres against attack by various atmospheric agents and by mechanical and chemical treatments generally applied to the skin and/or to the hair fibres.

The hydroxypropyl quaternary derivatives containing an ester function in accordance with the invention correspond to the formula (I):

$$R-\underset{\underset{O}{\|}}{C}-O-CH_2-CHOHCH_2-\overset{+}{N}\overset{R_1}{\underset{R_3}{\diagdown R_2}} \quad X^- \qquad (I)$$

in which:

R denotes a saturated or unsaturated, branched $C_7$–$C_{35}$ alkyl chain;

$R_1$, $R_2$ and $R_3$ independently denote a saturated or unsaturated, linear or branched $C_1$–$C_{18}$ alkyl chain;

$X^-$ denotes a halide or another anion chosen from:

$$R_4-O-\underset{\underset{O}{\|}}{\overset{\overset{O}{\|}}{S}}-O^-; \quad R_4-\underset{\underset{O}{\|}}{\overset{\overset{O}{\|}}{S}}-O^- \quad \text{and} \quad R_4-O-\underset{\underset{OR_5}{|}}{\overset{\overset{O}{\|}}{P}}-O^-$$

in which:

$R_4$ and $R_5$ independently denote a saturated or unsaturated, linear $C_1$–$C_8$ alkyl chain.

The preferred compounds of formula (I) are those corresponding to the following formula (I'):

$$R-\underset{\underset{O}{\|}}{C}-O-CH_2-CHOHCH_2-\overset{+}{N}\overset{CH_3}{\underset{CH_3}{\diagdown CH_3}} \quad Cl^- \qquad (I')$$

in which:

R denotes a saturated or unsaturated, branched $C_{11}$–$C_{23}$ alkyl chain.

Among these compounds, those most particularly preferred are chosen from [3-(2-octyl-dodecanoyloxy)-2-hydroxypropyl]trimethylammonium chloride;

[3-(2-decyltetradecanoyloxy)-2-hydroxypropyl] trimethylammonium chloride;

[3-(2-butyl-octanoyloxy)-2-hydroxypropyl] trimethylammonium chloride; and

[3-(2-hexyldecanoyloxy)-2-hydroxypropyl] trimethylammonium chloride.

The compounds of formula (I) of the invention can be prepared according to the following two-step process described in French Patent No. 1,313,143, the disclosure of which is specifically incorporated by reference herein:

(1) reacting an alkaline salt of a fatty aliphatic carboxylic acid with an epihalohydrin, in particular epichlorohydrin, and a secondary amine in an alcoholic solvent such as isopropanol or tert-butanol, and (2) separating the alkali metal halide formed and quaternizing the amino ester formed in the first step using an alkylating agent such as dimethylsulphate.

The compounds of formula (I) of the invention can also be prepared according to the two-step process described in U.S. Pat. No. 3,872,138, the is disclosure of which is specifically incorporated by reference herein:

(1) reacting a salt of a tertiary amine with a carboxylic acid in stoichiometric amounts in order to neutralize the acid with the amine, and (2) reacting the resulting salt with epichlorohydrin in a benzene-type solvent at a temperature of from 50 to 150° C. for a period of approximately 15 hours.

The compounds of formula (I) of the invention can more preferably be prepared according to a one-step process under simpler, faster, and safer implementation conditions than those of the two processes defined above, without using any epihalohydrin or any alkylating agents, which are generally toxic, or any highly toxic solvents.

This one-step process is described in the U.S. patent application entitled "Process for the Preparation of Hydroxypropylated Quaternary Ammoniurr Compounds Containing an Ester Functional Group," filed on the same day herewith in the name of Michel Philippe and Alain Campos, the disclosure of which is specifically incorporated by reference herein, which involves reacting, in a single stage and in an alcoholic solvent at reflux, an aliphatic carboxylic acid RCOOH salt, preferably a fatty aliphatic carboxylic acid RCOOH salt, or an aliphatic carboxylic acid, preferably a fatty aliphatic carboxylic acid, under basic catalysis conditions with a compound of formula (II):

$$CH_2\underset{O}{-}CH-CH_2-\overset{+}{N}\underset{R_3}{\overset{R_1}{-R_2}} \quad X^-\qquad(II)$$

in which R, $R_1$, $R_2$, $R_3$ and $X^-$ have the same meanings indicated in formula (I) above.

The carboxylic acid salt is preferably an alkali-metal or alkaline-earth metal salt of a carboxylic acid. Salts of an alkali metal such as sodium are particularly preferred. The basic catalysis is preferably carried out with sodium hydroxide, potassium hydroxide or triethylamine. The alcoholic solvent used is preferably chosen from lower $C_1$–$C_4$ alcohols and more particularly 2-butanol. The reaction temperature generally ranges from 45 to 150° C. and the reaction time preferably ranges from 4 to 8 hours. According to this process, the final product obtained at the end of the reaction can then be purified by simple washing and/or simple extraction using a solvent chosen, for example, from heptane, a lower $C_1$–$C_4$ alcohol such as methanol, or mixtures thereof.

Another subject of the invention is cosmetic or dermatological compositions containing at least one compound of formula (I) in a cosmetically acceptable medium.

The expression "cosmetically acceptable medium" is understood to refer to any medium which is compatible with keratin substances as a whole, such as the skin, the nails, mucous membranes and the hair or any other area of body skin.

The compositions of the invention contain the compounds of formula (I) preferably in concentrations ranging from 0.001 to 20% by weight, and more preferably from 0.05 to 15% by weight, relative to the total weight of the composition.

The compositions of the invention may also contain at least one additive chosen from thickeners, volatile or nonvolatile, soluble or insoluble silicones, surfactants, fragrances, pearlescent agents, preserving agents, sunscreens, proteins, vitamins, polymers, solvents commonly used in cosmetology or dermatology, plant, animal, mineral or synthetic oils and any other additive conventionally used in the cosmetic field.

These additives are present in the compositions according to the invention in proportions preferably ranging from 0 to 20% by weight, relative to the total weight of the composition. The precise amount of each additive is readily determined by a person skilled in the art on the basis of its nature and its, function.

Another subject of the invention is a process for treating the skin or keratin fibres, such as the hair, wherein a cosmetic composition as defined above is applied to the skin or to the keratin fibres, and then optionally rinsed with water.

Thus, this process according to the invention allows maintenance of the hairstyle and treatment, care or washing of the skin and the hair or of any other keratin substance.

The cosmetic compositions according to the invention can be in the form of a gel, a milk, a cream, a lotion, a solution which is relatively thickened, or a foam and can be used for the skin or the hair.

For the hair, the compositions are more particularly shampoos, rinse-out or leave-in compositions to be applied before or after a shampooing, dyeing, bleaching, permanent-waving or hair-straightening operation, or dyeing, bleaching, permanent-waving or straightening compositions for the hair.

The compositions can also be hairsetting lotions, blow-drying lotions or fixing lacquers and/or styling compositions. The lotions can be packaged in various forms, especially in vaporizers, pump-dispenser bottles or in aerosol containers in order to allow the composition to be applied in vaporized form or in the form of a foam. Such packaging forms are recommended, for example, when a spray, a lacquer or a foam for fixing or treating the hair is desired.

When a composition according to the invention is packaged in the form of an aerosol in order to obtain an aerosol lacquer or foam, it comprises at least one propellant which can be chosen from volatile hydrocarbons such as n-butane, propane, isobutane, pentane, chloro and/or fluoro hydrocarbons and mixtures thereof. Carbon dioxide, nitrous oxide, dimethyl ether, nitrogen or compressed air can also be used as a propellant.

A further subject of the invention is the use of the compounds of formula (I) as defined above as a hair conditioner in the preparation of a haircare and/or hair treatment formulation, and more particularly as an agent for improving the smoothness, combing and disentangling of the hair.

Hereinabove and hereinbelow, the percentages are expressed on a weight basis.

The invention will now be illustrated more fully with the aid of the examples which follow, which should not be considered as limiting it to the embodiments described.

In the examples, AM means active material.

PREPARATION EXAMPLES

Example 1

Preparation of [3-(2-octyl-dodecanoyloxy)-2-hydroxypropyl]-trimethylammonium chloride $$R-\overset{O}{\underset{\|}{C}}-O-CH_2-CHOHCH_2-\overset{+}{N}\underset{CH_3}{\overset{CH_3}{-CH_3}} \quad Cl^-\qquad(I)$$

with $$R = CH_3-(CH_2)_9-\underset{C_8H_{17}}{CH-}$$

The following ingredients:

100 ml of 2-butanol, 0.15 mol of 2-octyldodecanoic acid (46.5 g), and 0.075 mol of sodium hydrogen carbonate (0.63 g)

were introduced into a round-bottomed flask fitted with a stirrer, a thermometer, a dropping funnel and a vertical condenser.

The mixture was heated to the reflux temperature of the 2-butanol (98–99° C.). As soon as the hydrogen carbonate dissolved in the medium, 0.15 mol (22.7 g) of glycidyltrimethylammonium chloride dissolved in 50 ml of 2-butanol was introduced dropwise. Refluxing was maintained for 6 hours after the end of the introduction.

The reaction medium was washed with water and then with heptane. The upper phase was concentrated to dryness and then taken up in a heptane/methanol/water mixture. The lower phase was concentrated to dryness. An amber-colored paste was obtained.

Analyses

Chloride number: 1.95 meq/g

Acid number: 0.43 meq/g, i.e. 19% acid (on a molar basis)

| | Elemental analysis | |
|---|---|---|
| | Found | Theory +19% acid +1H$_2$O |
| C | 65.8 | 66.06 |
| H | 11.65 | 11.75 |
| N | 2.86 | 2.53 |
| O | 13.63 | 12.94 |
| Cl$^-$ | 6.43 | 6.55 |

Example 2

Preparation of [3-(2-decyltetra-decanoyloxy)-2-hydroxypropyl]-trimethylammonium chloride

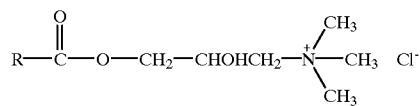 (I)

with

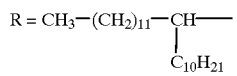

The following ingredients:

100 ml of 2-butanol, 0.15 mol of 2-decyltetradecanoic acid (36.8 g), and 0.075 mol of sodium hydrogen carbonate (0.63 g)

were introduced into a round-bottomed flask fitted with a stirrer, a thermometer, a dropping funnel and a vertical condenser.

The mixture was heated to the reflux temperature of the 2-butanol (98–99° C.). As soon as the hydrogen carbonate dissolved in the medium, 0.15 mol (22.7 g) of glycidyltrimethylammonium chloride dissolved in 50 ml of 2-butanol was introduced dropwise. Refluxing was maintained for 6 hours after the end of the introduction.

The reaction medium was washed with water and then with heptane. The upper phase was concentrated to dryness and then taken up in a heptane/methanol/water mixture. The lower phase was concentrated to dryness.

A pale yellow paste was obtained.

Analyses

Chloride number: 1.71 meq/g

Acid number: 0.174 meq/g, i.e. 10% acid (on a molar basis)

| | Elemental analysis | |
|---|---|---|
| | Found | Theory +10% acid +1H$_2$O |
| C | 66.72 | 66.6 |
| H | 12.06 | 12.4 |
| N | 2.62 | 2.4 |
| O | 13.35 | 12.9 |
| Cl$^-$ | 6.03 | 6.08 |

Example 3

Preparation of [3-(2-butyloctanoyloxy)-2-hydroxypropyl]trimethylammonium chloride

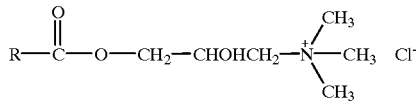 (I)

with

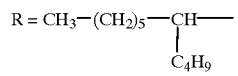

The following ingredients:

100 ml of 2-butanol, 0.15 mol of 2-butyloctanoic acid (30 g), and 0.075 mol of sodium hydrogen carbonate (0.63 g)

were introduced into a round-bottomed flask fitted with a stirrer, a thermometer, a dropping funnel and a vertical condenser.

The mixture was heated to the reflux temperature of the 2-butanol (98–99° C.). As soon as the hydrogen carbonate dissolved in the medium, 0.15 mol (22.7 g) of glycidyltrimethylammonium chloride dissolved in 50 ml of 2-butanol was introduced dropwise. Refluxing was maintained for 6 hours after the end of the introduction.

The reaction medium was washed with water and then with heptane. The upper phase was concentrated to dryness and then taken up in a heptane/methanol/water mixture. The lower phase was concentrated to dryness. An amber-colored paste was obtained.

Analyses

Chloride number: 2.60 meq/g

Acid number: 0.11 meq/g, i.e. 4.2% acid (on a molar basis)

| | Elemental analysis | |
|---|---|---|
| | Found | Theory +4.2% acid +1H$_2$O |
| C | 58.5 | 57.5 |
| H | 11.03 | 10.9 |
| N | 3.83 | 3.5 |

| | Elemental analysis | |
|---|---|---|
| | Found | Theory +4.2% acid +1H$_2$O |
| O | 18.54 | 18.8 |
| Cl$^-$ | 8.59 | 9.0 |

Example 4

Preparation of [3-(2-hexyldecanoyloxy)-2-hydroxypropyl]trimethylammonium chloride

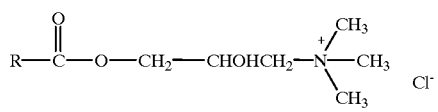 (I)

with

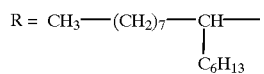

The following ingredients:

100 ml of 2-butanol, 0.15 mol of 2-hexyldecanoic acid (38.4 g), and 0.075 mol of sodium hydrogen carbonate (0.63 g)

were introduced into a round-bottomed flask fitted with a stirrer, a thermometer, a dropping funnel and a vertical condenser.

The mixture was heated to the reflux temperature of the 2-butanol (98–99° C.). As soon as the hydrogen carbonate dissolved in the medium, 0.15 mol (22.7 g) of glycidyltrimethylammonium chloride dissolved in 50 ml of 2-butanol was introduced dropwise. Refluxing was maintained for 6 hours after the end of the introduction.

The reaction medium was washed with water and then with heptane. The upper phase was concentrated to dryness and then taken up in a heptane/methanol/water mixture. The lower phase was concentrated to dryness. An amber-colored paste was obtained.

Analyses

Chloride number: 1.98 meq/g

Acid number: 0.066 meq/g, i.e. 3.3% acid (on a molar basis)

| | Elemental analysis | |
|---|---|---|
| | Found | Theory +3.3% acid +1H$_2$O |
| C | 56.1 | 56.6 |
| H | 11.15 | 11.21 |
| N | 3.5 | 2.93 |
| O | 22.1 | 21.6 |
| Cl$^-$ | 6.91 | 7.44 |

APPLICATION EXAMPLE

Example A

Shampoo

| | |
|---|---|
| Sodium lauryl ether sulphate. | 12 g |
| Compound of Example 4 | 0.5 g A.M. |
| Dyes, fragrances, preserving agents | qs |
| Water pH adjusted to 7 qs | 100 g |

This shampoo had good foaming power and improved the disentangling and softness of the hair.

We claim:

1. A method for improving the smoothness, combing and/or disentangling of hair, said method comprising applying to said hair an effective amount of a haircare composition comprising at least one hydroxypropyl quaternary ammonium compound containing an ester function, said compound having the formula (I):

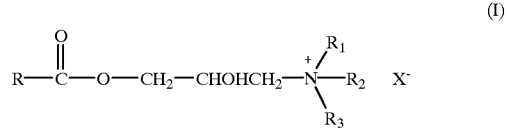 (I)

in which:

R denotes a saturated or unsaturated, branched C$_7$–C$_{35}$ alkyl chain;

R$_1$, R$_2$ and R$_3$ independently denote a saturated or unsaturated, linear or branched C$_1$–C$_{18}$ alkyl chain; and X$^-$ denotes a halide or another anion, said anion being:

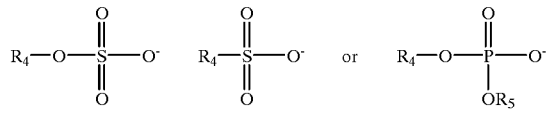

in which R$_4$ and R$_5$ independently denote a saturated or unsaturated, linear or branched C$_1$–C$_8$ alkyl chain.

* * * * *